United States Patent [19]

Shoda

[11] 4,220,995
[45] Sep. 2, 1980

[54] APPARATUS FOR DETECTING TIP DAMAGES OF A MILLING CUTTER

[75] Inventor: Hiroshi Shoda, Kaga, Japan

[73] Assignee: Kabushiki Kaisha Komatsu Seisakusho, Tokyo, Japan

[21] Appl. No.: 946,555

[22] Filed: Sep. 28, 1978

[30] Foreign Application Priority Data

May 30, 1978 [JP] Japan .................. 53/63808

[51] Int. Cl.² .................. G06F 15/46; G01N 3/58
[52] U.S. Cl. .................. 364/508; 73/104; 340/683; 364/474; 364/511
[58] Field of Search .......... 364/474, 508, 511, 483, 364/472; 73/104, 105, 112, 116, 570, 658, 660; 83/62, 62.1, 72; 340/679, 683; 72/6, 8, 19, DIG. 29; 90/11 R, DIG. 7; 409/79, 80, 133, 134, 148, 194

[56] References Cited

U.S. PATENT DOCUMENTS

| | | | |
|---|---|---|---|
| 3,809,870 | 5/1974 | Auble et al. .................. 364/511 |
| 3,839,628 | 10/1974 | Higgins et al. .................. 364/511 X |
| 3,841,149 | 10/1974 | Edwin et al. .................. 73/104 X |
| 3,848,115 | 11/1974 | Sloane et al. .................. 364/508 |
| 3,991,984 | 11/1976 | Porter .................. 364/511 X |
| 4,087,801 | 5/1978 | Noh .................. 73/658 X |

*Primary Examiner*—Joseph F. Ruggiero
*Attorney, Agent, or Firm*—Armstrong, Nikaido, Marmelstein & Kubovcik

[57] ABSTRACT

An apparatus for detecting tip damages of a milling cutter comprising a motor for driving the milling cutter, a vibration detector mounted on the milling cutter, a vibration increase calculating device connected with the vibration detector for calculating vibration increase at every preset time, an abnormal vibration increase preset device, a comparator connected with the vibration increase calculating device and with the abnormal vibration increase preset device for comparing the output signals thereof, a memory connected with the comparator for storing abnormal signal from the comparator, and a gate connected with the comparator and with the memory wherein the gate is adapted to send out cutter abnormal condition indicating signals as an output only when both output signals from the comparator and the memory are abnormal.

10 Claims, 8 Drawing Figures

APPARATUS FOR DETECTING TIP DAMAGES OF A MILLING CUTTER

BACKGROUND OF THE INVENTION

This invention relates to an apparatus for detecting tip damages of a milling cutter for use in a crank-shaft miller. A crank-shaft is cut by rotating it in contact with a cutter miller which is also rotated and moved while keeping its contact with the crank-shaft.

Generally, a plurality of tips are mounted on the outer periphery of the cutter body to cut a crank-shaft. If one tip is damaged, the subsequent tip must cut a part of a crank-shaft assigned thereto plus a part assigned to the damaged tip, and therefore it is required for the subsequent tip to resist a double cutting load imposed thereon.

Therefore, if one tip is damaged while the milling cutter is in operation, other tips tend to be damaged by a chain reaction and eventually all tips tend to be damaged if cutting operation is continued.

SUMMARY OF THE INVENTION

It is therefore an object of the present invention to provide a crank-shaft miller provided with an apparatus for detecting tip damages of a milling cutter.

Another object of the present invention is to provide an apparatus for detecting damages of tips of a milling cutter wherein damages of one or two tips can easily be detected and located thereby preventing other tips from being damaged.

In accordance with an aspect of the present invention, there is provided an apparatus for detecting tip damages of a milling cutter which comprises vibration detecting means mounted on the milling cutter, vibration increase calculating means connected with said vibration detecting means for calculating increases in vibration at every preset time, abnormal vibration increase preset means, comparator means connected with said vibration increase calculating means and with said abnormal vibration increase preset means for comparing output signals thereof, memory means connected with said comparator means for storing abnormal signals from said comparator means, and gate means connected with said comparator means and with said memory means, said gate means being adapted to send out cutter abnormal indicating signals as an output only when both output signals from said comparator means and said memory means are abnormal.

According to another aspect of the present invention, the vibration detector means is replaced by an electric power detecting means. All the remaining elements thereof are similar to those of the first embodiment but modified to receive electric power increase inputs instead of receiving vibration increase inputs.

The above and other objects, features and advantages of the present invention will be readily apparent from the following description taken in conjunction with the accompanying drawings.

DETAILED DESCRIPTION OF THE INVENTION

Figure 1:
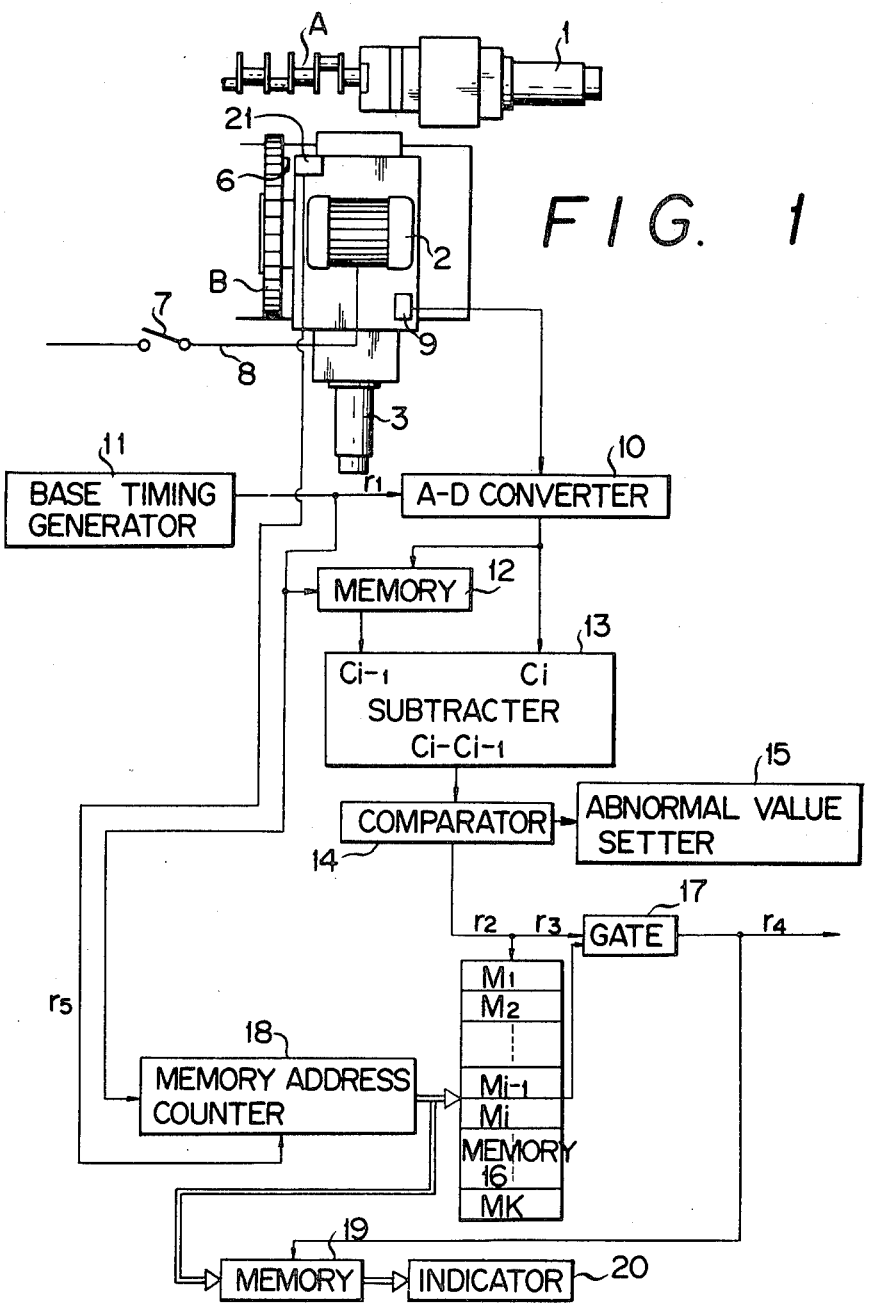
FIG. 1 is a block diagram of one embodiment of the present invention.

The present invention will now be described by way of embodiments only with reference to the accompanying drawings.

Reference numeral 1 denotes X-axis servo motor for driving or rotating a crank-shaft "A", and 2 a motor for driving or rotating a milling cutter "B", said motor 2 being adapted to be fed or moved towards the crank-shaft "A" by means of a Y-axis servo motor 3.

Figure 2:
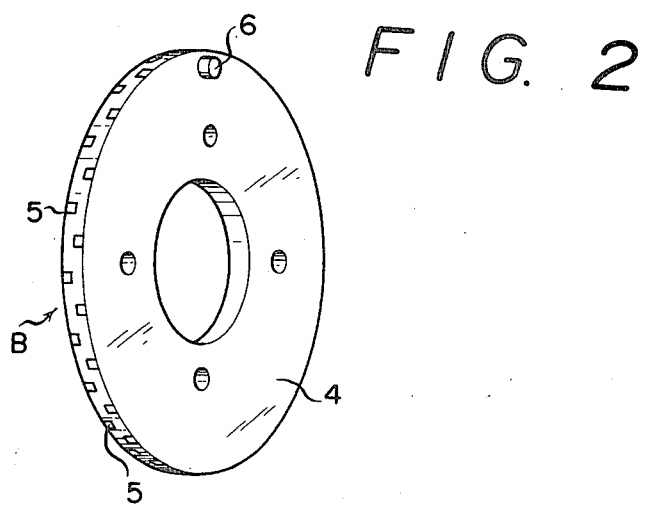
FIG. 2 is a perspective view of a milling cutter employed in the present invention.

The milling cutter "B" comprises as shown in FIG. 2 a plurality of tips 5 mounted on the peripheral surface of a disk-shaped cutter body 4, the cutter body 4 having a cutter's reference position detecting dog 6 mounted thereon.

When a switch 7 is turned on, the above-mentioned motor 2 is electrically connected with a power supply by way of a power line 8 and is consequently driven or rotated.

Reference numeral 9 denotes a vibration detector mounted on a main shaft head secured in vicinity of the motor 2, said vibration detector being adapted to detect an abnormal vibration caused by a damage of tip 5 of the milling cutter "B". The vibration input detected by the vibration detector 9 is sent to an analogue-digital (A-D) converter which is adapted to convert the analogue quantity shown by a curve "C" into the digital quantity shown by "D".

Stating more specifically, a signal $r_1$ sent from a base timing generator 11 converts the vibration input from the analogue quantity "C" into digital quantity "D" at a frequency of $T_1$ to $T_N$ during one revolution of the milling cutter "B". In the illustrated embodiment, arrangement is made such that the vibration input is converted from the analogue quantity into the digital quantity by the number corresponding to those of the tips 5, and the vibration input when cutting a workpiece by each tip 5 can be detected as digital quantity "D".

The output side of the A-D converter 10 is connected with a vibration input memory 12 and a subtracter 13. The subtracter 13 is adapted to subtract the output of the vibration input memory 12 from that of the A-D converter 10, and upon completion of the subtraction, the output from the A-D converter is stored in the vibration input memory 12.

Figure 3:
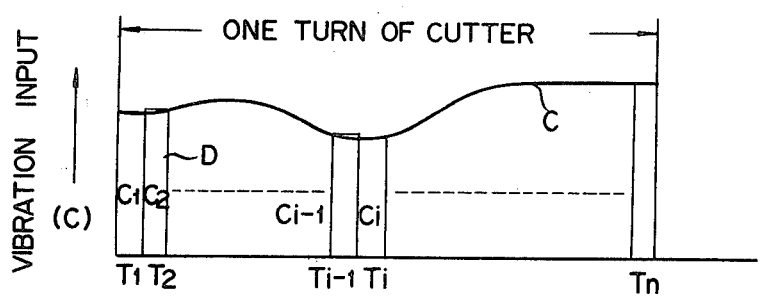
FIG. 3 is a diagram showing analogue-digital conversion of vibration inputs.

Stating in more detail, when the subtraction is made by the subtracter 13, data older than the output of the A-D converter 10 by one is stored in the vibration input memory 12. Referring to FIG. 3, when data $C_i$ at the time $T_i$ is sent out by the A-D converter 10 as an output, data $C_{i-1}$ at the time $T_{i-1}$ is stored in the vibration input memory 12 and subtraction $(C_i - C_{i-1})$ is made by the subtracter 13. After the completion of the operation, the data $C_i$ at the time $T_i$ is stored in the vibration input memory 12, and substraction $(C_{i+1} - C_i)$ is made by the subtractor 13. In other words, the increase in the vibration input (vibration caused by the cutting operation of tips 5) per unit time is detected.

The output of the subtractor 13 is sent to a comparator 14 which is adapted to compare the output of the subtracter 13 (the vibration increase) with that of an abnormal value setter 15 (the limit of vibration increase). The comparator 15 sends out an abnormal condition indicating signal $r_2$ as an output if the output of the subtractor 13 is higher than that of the setter 15, and sends out a normal signal $r_3$ as an output if the output of the subtractor 13 is equal to or less than that of the setter 15. The output is then sent to a cutter's abnormal condition discriminating or detecting gate 17.

Further, the relationship wherein the output of the subtractor 13 is higher than that of the setter 15 is sometimes established due to the material of the workpiece etc, and in this case abnormal condition indicating signal $r_2$ is sent out as an output. In such a case, to discriminate it from the case of tip damages, the output of the comparator 14 is stored in an abnormal condition indicating signal storing memory 16. Such storage or memory is of course made by a memory address counter 18 synchronizing with the afore-mentioned base timing generator 11. Stated more specifically, the output of the comparator 14 at the time $T_i$ is stored in a unit memory $M_i$ of the memory 16, and the output of the comparator 14 at the time $T_{i+1}$ is stored in a unit memory $M_{i+1}$ of the memory 16.

The outputs stored in unit memories $M_1$ to $M_k$ of the cutter abnormal condition storing memory 16 are sent to the cutter abnormal condition discriminating gate 17 at the same time as the first one revolution, when measured from the revolution reference point after the milling cutter has been rotated by one revolution. The cutter abnormal condition discriminating gate 17 is adapted to send out a cutter abnormal condition indicating signal $r_4$ only when both the output sent out by the cutter abnormal condition storing memory 16 and the output of the comparator 14 are abnormal condition indicating signals $r_2$.

Figure 4:
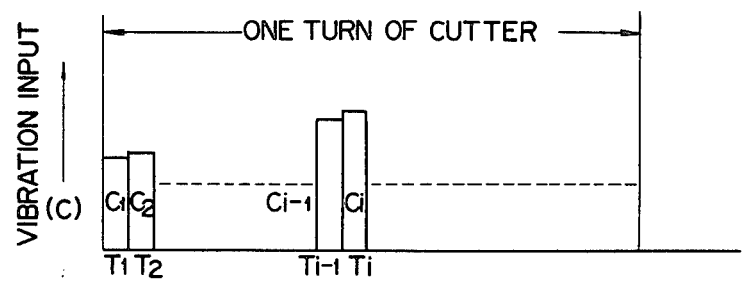
FIGS. 4 to 7 are diagrams explaining the operation of the present invention.
Figure 6:
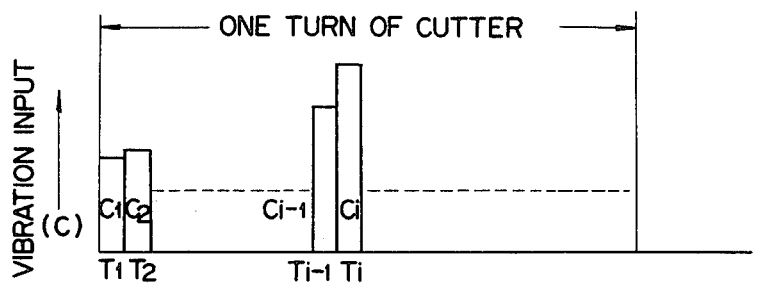
Figure 5:
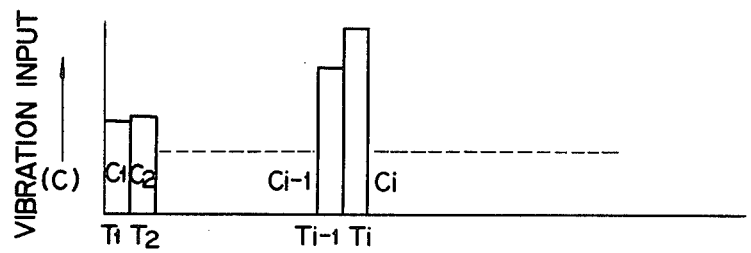
Figure 7:
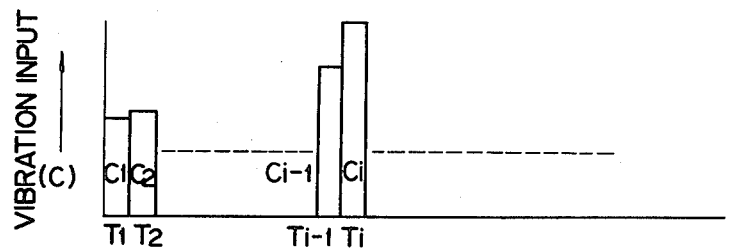

The operation of the present invention will now be described with reference to FIGS. 4, 5, 6 and 7. In FIG. 4, the output of the comparator 14 at the time $T_i$ is a normal signal $r_3$ ($C_i - C_{i-1} \leqq$ the output of the setter). Even if the output of the comparator 14 at the time $T_i$ after the milling cutter "B" has been rotated by one revolution is an abnormal signal $r_2$ ($C_i - C_{i-1} >$ the output of the setter) as shown in FIG. 5, no cutter abnormal condition indicating signal $r_4$ is generated. Further, as shown in FIGS. 6 and 7, when both the output of the comparator 14 at the time $T_i$ and the output thereof at the time $T_i$ after the milling cutter has been rotated by one revolution are abnormal signals $r_2$ ($C_i - C_{i-1} >$ the output of the setter), a cutter abnormal condition indicating signal $r_4$ is sent out as an output.

Further, because the milling cutter "B" includes a plurality of tips 5 mounted on the cutter body 4, it is difficult to identify which tip is damaged so as to send out an abnormal condition indicating signal $r_4$. For this reason, the value of the memory address counter 18 for counting the number of timing pulses of the base timing generator 11 is stored in a cutter's abnormal position storing memory 19 so as to send out an output to a cutter abnormal position indicator 20 based on the value obtained when the cutter abnormal condition discriminating gate 17 sends out a cutter abnormal condition indicating signal $r_4$ as an output thereby enabling damaged tip or tips 5 to be indicated or detected easily.

Further, reference numeral 21 indicates a cutter's one revolution detector switch mounted against the cutter reference position detecting dog 6 mounted on the cutter body 4. The detector switch 21 generates a detection signal $r_5$ which restores the memory address counter 18 into the initial condition so as to synchronize the cutter abnormal condition storing memory 16 with the milling cutter "B".

As described hereinabove, since the cutter abnormal condition discriminating gate 17 will send out a cutter abnormal condition indicating signal $r_4$ as an output if one of the tips 5 is damaged, it can be detected without fail that one of the tips 5 is damaged or broken.

Further, the gate 17 will generate a cutter abnormal condition indicating signal $r_4$ when the milling cutter has been continuously rotated by two revolutions so as to generate an abnormal signal $r_2$ as an output at the same tip 5. Therefore, even if an abnormal condition indicating signal $r_2$ is generated as an output by some reason at a time when the milling cutter is rotated by one revolution, no cutter abnormal condition indicating signal $r_4$ is generated as an output.

Accordingly, the possibility of generation of cutter abnormal condition indicating signal $r_4$ due to wrong operations etc. can be eliminated, and the failure or damage of a tip or tips 5 of the milling cutter "B" can be detected without fail.

Further, since the position of damaged tip 5 can be indicated by the indicator 20, the position of the broken tip 5 can be detected very easily.

Figure 8:
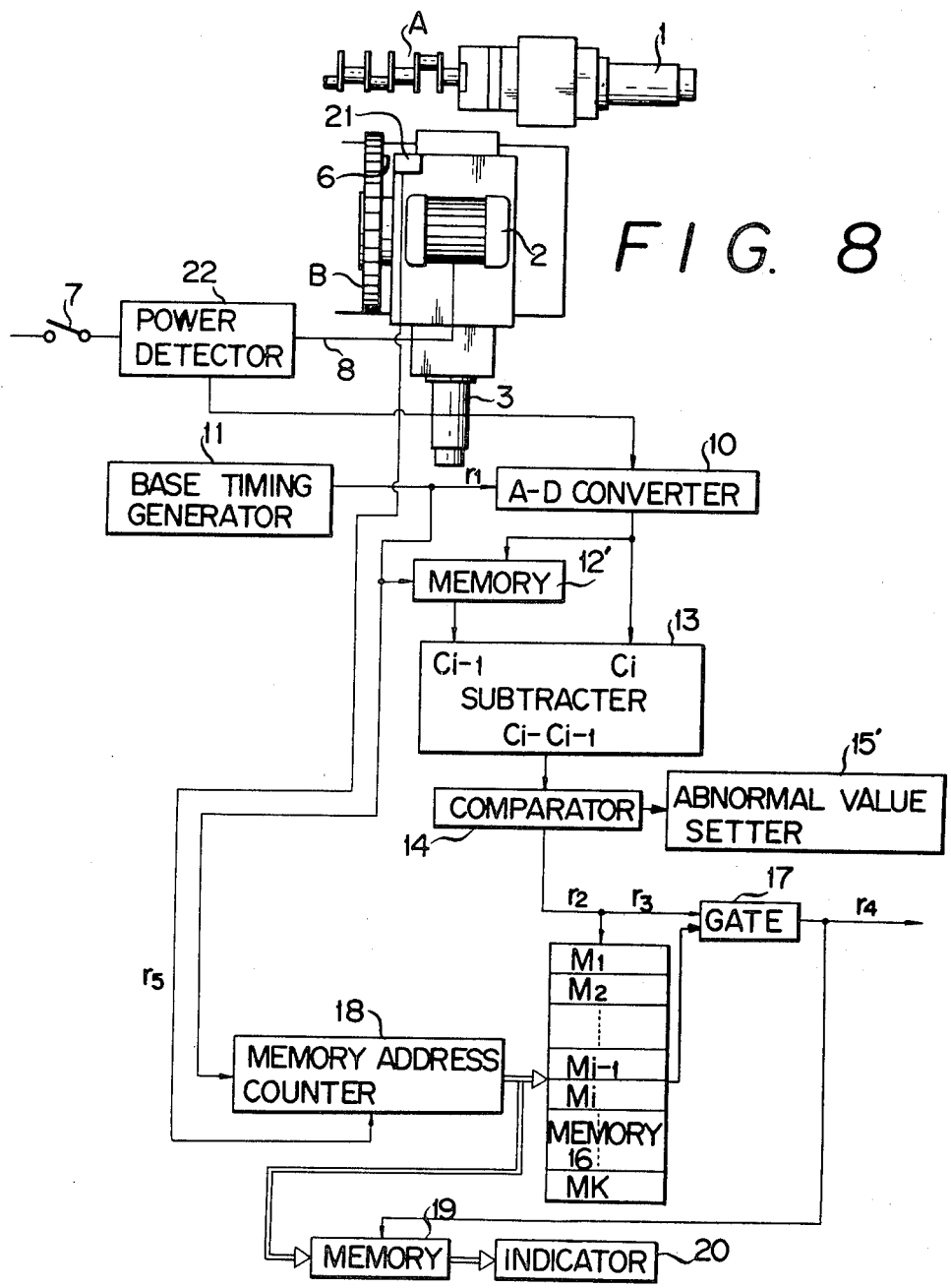
FIG. 8 is similar to FIG. 2 but showing another embodiment of the present invention employing an electric power input detector.

Referring to FIG. 8 showing another embodiment of the present invention, arrangement is made such that variations in the input power supplied to the motor 2 to drive the milling cutter "B" can be detected instead of detecting the vibration of the milling cutter.

Stating in more detail, a motor input detector 22 is connected with the power supply line 8. The motor input detector 22 is adapted to detect the power variation by converting the power into voltage, and the voltage detected thereby is sent to the A-D converter 10 so as to be converted from analog quantity to digital quantity. The other operations of this device is similar to those of the first embodiment already described with reference to FIG. 1, and therefore its description is omitted.

In this embodiment, reference numeral 12' denotes a motor input storing memory and 15' an abnormal electric power setter.

Since various changes and modification of the present invention will occur to and can be made readily by those skilled in the art without departing from the invention concept, the invention is not to be taken as limited except by the scope of the appended claims.

What is claimed is:

1. An apparatus for detecting tip damages of a milling cutter comprising vibration detector means mounted on the milling cutter;
   vibration increase calculating means connected to said vibration detector means for calculating increases in vibration at every preset time;
   abnormal vibration increase preset means;
   comparator means connected with said vibration increase calculating means and with said abnormal vibration increase preset means for comparing output signals thereof;
   first memory means connected with said comparator means for storing abnormal condition indicating signals from said comparator means; and
   gate means connected with said comparator means and with said first memory means, said gate means being adapted to send out cutter abnormal condition indicating signals as an output only when both output signals from said comparator means and said first memory means are abnormal.

2. The apparatus for detecting tip damages of a milling cutter as defined in claim 1 wherein said vibration increase calculating means comprises subtracting means and second memory means having an output connected with said subtracting means.

3. The apparatus for detecting tip damages of a milling cutter as defined in claim 1 or 2, further comprising analogue-digital converter means disposed between said vibration detector means and said calculating means, and base timing generator means connected with said analogue-digital converter means and with said calculating means.

4. The apparatus for detecting tip damages of a milling cutter as defined in claim 3, further comprising memory address counter means, the input of said memory address counter means being connected to said base timing generator means and the output of said memory address counter means being connected to said first memory means.

5. The apparatus for detecting tip damages of a milling cutter as defined in claim 4, further comprising third memory means for storing cutter abnormal positions, said third memory means being connected with said memory address counter means and with said gate means and, cutter abnormal position display means connected with said third memory means.

6. An apparatus for detecting tip damages of a milling cutter comprising a motor for driving the milling cutter;
electric power detector means connected with said motor;
power increase calculating means connected with said electric power detector means for calculating electric power increase at every preset time;
abnormal power increase preset means;
comparator means connected with said power increase calculating means and with said abnormal power increase preset means for comparing output signals thereof;
first memory means connected with said comparator means for storing abnormal condition indicating signals from said comparator means; and gate means connected with said comparator means, said gate means and said first memory means being adapted to send out cutter abnormal condition indicating signals as an output only when both output signals from said comparator means and said first memory means are abnormal.

7. The apparatus for detecting tip damages of a milling cutter as defined in claim 6, wherein said power increase calculating means comprises subtracting means and second memory means having an output connected to said subtracting means.

8. The apparatus for detecting tip damages of a milling cutter as defined in claim 6 or 7, further comprising analogue-digital converter means disposed between said electric power detector means and said calculating means, and base timing generator means connected with said analogue-digital converter means and with said calculating means.

9. The apparatus for detecting tip damages of a milling cutter as defined in claim 8, further comprising memory address counter means, the input of said memory address counter means being connected to said base timing generator means and the output of said memory address counter means being connected to said first memory means.

10. The apparatus for detecting tip damages of a milling cutter as defined in claim 9, further comprising third memory means for storing cutter abnormal positions, said third memory means being connected with said memory address counter means and with said gate means, and cutter abnormal position display means connected with said third memory means.

* * * * *